United States Patent
Taylor

(10) Patent No.: US 9,664,657 B2
(45) Date of Patent: May 30, 2017

(54) PULSED ADMISSION OF ANALYTE TO DETECTION APPARATUS

(71) Applicant: Smiths Detection-Watford Limited, Watford, Hertfordshire (GB)

(72) Inventor: Stephen John Taylor, Hyde Heath (GB)

(73) Assignee: Smiths Detection—Watford Limited, Watford, Hertfordshire (GB)

(*) Notice: Subject to any disclaimer, the term of this patent is extended or adjusted under 35 U.S.C. 154(b) by 345 days.

(21) Appl. No.: 14/284,449

(22) Filed: May 22, 2014

(65) Prior Publication Data

US 2014/0287522 A1    Sep. 25, 2014

Related U.S. Application Data

(62) Division of application No. 12/521,542, filed as application No. PCT/GB2007/004711 on Dec. 10, 2007, now Pat. No. 8,734,722.

(30) Foreign Application Priority Data

Dec. 20, 2006  (GB) .................................. 0625478.3

(51) Int. Cl.
*G01N 33/00* (2006.01)
*G01N 27/62* (2006.01)

(52) U.S. Cl.
CPC ....... *G01N 33/0004* (2013.01); *G01N 27/622* (2013.01); *Y10T 436/24* (2015.01); *Y10T 436/25875* (2015.01)

(58) Field of Classification Search
CPC  G01N 33/0004; G01N 27/622; Y10T 436/24; Y10T 436/25875
See application file for complete search history.

(56) References Cited

U.S. PATENT DOCUMENTS 3,107,966 A    10/1963  Bonhomme
3,461,285 A     8/1969  Werner et al.
(Continued)

FOREIGN PATENT DOCUMENTS

EP    0135747    4/1985
GB    2323165    9/1998
(Continued)

OTHER PUBLICATIONS

Snyder, A. Peter et al. "Portable hand-held gas chromatography/IMS device." Analytical Chemistry (1993) 65 299-306.*
(Continued)

*Primary Examiner* — Christopher A Hixson
(74) *Attorney, Agent, or Firm* — Reinhart Boerner Van Deuren s.c.

(57) ABSTRACT

A detecting method using an IMS apparatus with a preconcentrator outside its inlet aperture. Analyte vapor is adsorbed during a first phase when substantially no gas is admitted to the reaction region. The preconcentrator is then energized to desorb the analyte molecules and create a volume of desorbed molecules outside the IMS housing. Next, a pressure pulser is energized momentarily to drop pressure in the housing and draw in a small sip of the analyte molecules from the desorbed volume through the aperture. This is repeated until the concentration of analyte molecules in the desorbed volume is too low for accurate analysis, following which the apparatus enters another adsorption phase.

18 Claims, 1 Drawing Sheet

(56) References Cited

U.S. PATENT DOCUMENTS

| | | |
|---|---|---|
| 3,470,527 A | 9/1969 | Bonhomme |
| 3,787,681 A | 1/1974 | Brunnee et al. |
| 4,378,499 A | 3/1983 | Spangler et al. |
| 4,551,624 A | 11/1985 | Spangler et al. |
| 5,083,019 A | 1/1992 | Spangler |
| 5,227,628 A | 7/1993 | Turner |
| 5,304,797 A | 4/1994 | Irie et al. |
| 5,574,277 A | 11/1996 | Taylor |
| 5,723,861 A | 3/1998 | Carnahan et al. |
| 5,834,771 A * | 11/1998 | Yoon .................. G01N 27/622 250/286 |
| 5,854,431 A | 12/1998 | Linker et al. |
| 5,952,652 A | 9/1999 | Taylor et al. |
| 6,051,832 A | 4/2000 | Bradshaw |
| 6,073,498 A | 6/2000 | Taylor |
| 6,102,746 A | 8/2000 | Nania et al. |
| 6,225,623 B1 | 5/2001 | Turner et al. |
| 6,239,428 B1 | 5/2001 | Kunz |
| 6,442,997 B1 | 9/2002 | Megerle |
| 6,459,079 B1 | 10/2002 | Machlinski et al. |
| 6,481,263 B1 | 11/2002 | Haley |
| 6,495,824 B1 | 12/2002 | Atkinson |
| 6,502,470 B1 | 1/2003 | Taylor et al. |
| 6,523,393 B1 | 2/2003 | Linker et al. |
| 6,825,460 B2 | 11/2004 | Breach et al. |
| 6,992,284 B2 | 1/2006 | Schultz et al. |
| 7,098,449 B1 | 8/2006 | Miller et al. |
| 7,118,712 B1 | 10/2006 | Manginell |
| 7,311,566 B2 | 12/2007 | Dent |
| 2002/0150923 A1 | 10/2002 | Malik |
| 2004/0259265 A1 | 12/2004 | Bonne |
| 2005/0017163 A1 | 1/2005 | Miller et al. |
| 2005/0095722 A1 | 5/2005 | McGill et al. |
| 2005/0109932 A1 | 5/2005 | Mullock et al. |
| 2005/0161596 A1 | 7/2005 | Guevremont et al. |
| 2005/0178975 A1 | 8/2005 | Glukhoy |
| 2005/0253061 A1 | 11/2005 | Cameron et al. |
| 2006/0249673 A1 | 11/2006 | Breach et al. |

FOREIGN PATENT DOCUMENTS

| | | |
|---|---|---|
| WO | 9301485 | 1/1993 |
| WO | 9322033 | 11/1993 |
| WO | 9921212 | 4/1999 |
| WO | 0079261 | 12/2000 |
| WO | 0195999 | 12/2001 |
| WO | 02078047 | 10/2002 |
| WO | 2004012231 | 2/2004 |
| WO | 2006046077 | 5/2006 |
| WO | 2008035095 | 3/2008 |

OTHER PUBLICATIONS

Tian, Wei-Cheng et al. "Multiple-stage microfabriated preconcentrator-focuser for micro gas chromatography system." Journal of Microelectromechanical Systems (2005) 14 498-507.*

Creaser, Colin S. et al.: "Ion mobility spectrometry: a review. Part 1. Structural analysis by mobility measurement." The Analyst (2004) 129 984-994.

Ritter, Leah S. et al.: "Solid phase micro-extraction in a miniature ion trap mass spectrometer." The Analyst (2003) 128 1119-1122.

Jiao, Charles Q. et al.: "A pulsed-leak valve for use with ion trapping mass spectrometers." J Am Soc Mass Spectrom (1996) 7 118++-122.+.

* cited by examiner

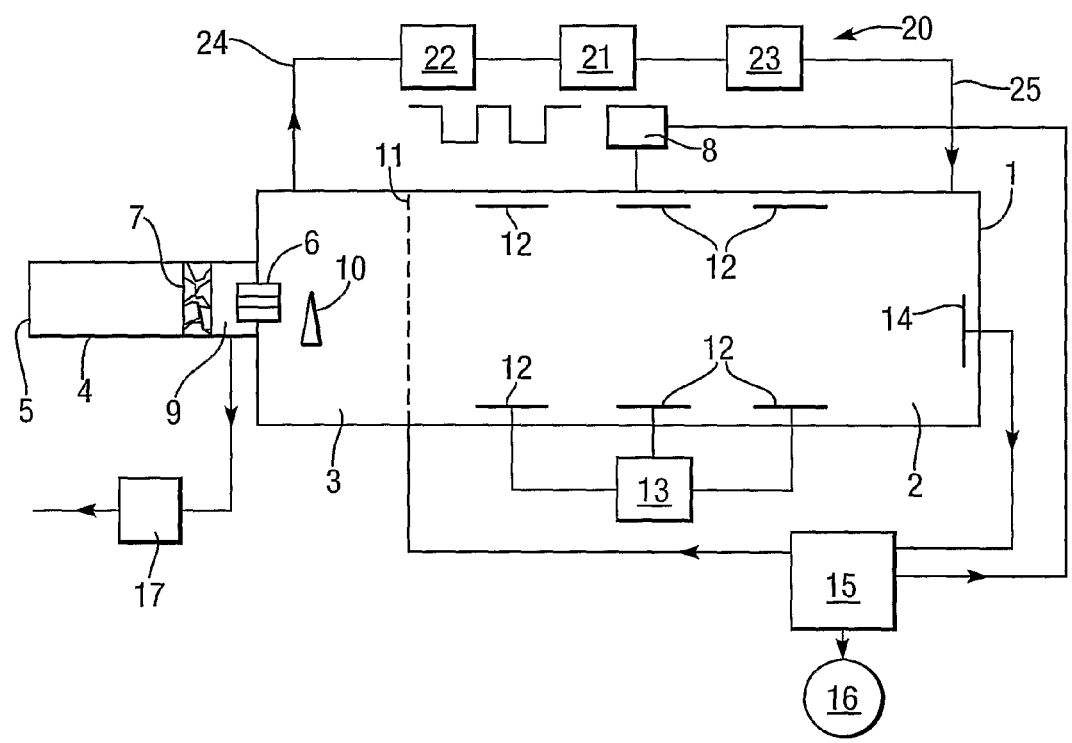

PULSED ADMISSION OF ANALYTE TO DETECTION APPARATUS

IDENTIFICATION OF RELATED PATENT APPLICATIONS

This patent application is a division of U.S. patent application Ser. No. 12/521,542, filed on Jun. 26, 2009, entitled "Detection Apparatus Accompanying Preconcentrator Pulsed Analyte Via An Aperture," now U.S. Pat. No. 8,734,722, granted on May 27, 2014, which is a U.S. National Stage patent application under 35 U.S.C. Section 371 of PCT International Patent Application No. PCT/GB2007/004711, filed on Dec. 10, 2007, which in turn claims priority of Great Britain Patent Application No. 0625478.3, filed on Dec. 20, 2006, all of which are assigned to the assignee of the present patent application and all of which are hereby incorporated herein by reference in their entirety.

This application is related to three other patents, namely U.S. Pat. No. 8,668,870, granted on Mar. 11, 2014, entitled "Ion Mobility Spectrometer Which Controls Carrier Gas Flow to Improve Detection," U.S. Pat. No. 8,158,933, granted on Apr. 17, 2012, entitled "Detector Apparatus and Preconcentrators," and U.S. Pat. No. 8,022,360, granted on Sep. 20, 2011, entitled "Gas Preconcentrator for Detection Apparatus," all assigned to the assignee of the present patent application, which three patents are hereby incorporated herein by reference.

BACKGROUND OF THE INVENTION

Field of the Invention

This invention relates to detection apparatus of the kind for detecting or analyzing an analyte sample gas or vapor, the apparatus having an aperture through which analyte sample gas or vapor is admitted.

Ion mobility spectrometers or IMS apparatus are often used to detect substances such as explosives, drugs, blister and nerve agents, or the like. An IMS apparatus typically includes a detector cell to which a sample of air containing a suspected substance or analyte is continuously supplied as a gas or vapor. The cell operates at or near atmospheric pressure and contains electrodes energized to produce a voltage gradient along the cell. Molecules in the sample of air are ionized, such as by means of a radioactive source, UV source, or by corona discharge, and are admitted into the drift region of the cell by an electrostatic gate at one end. The ionized molecules drift to the opposite end of the cell at a speed dependent on the mobility of the ions. By measuring the time of flight along the cell, it is possible to identify the ions. In conventional IMS apparatus clean dry gas flows continuously through the reaction or ionization region. This arrangement allows for continuous sampling and short recovery times. Where the sample analyte is only present in small concentrations in the sample gas, there can be a relatively low signal-to-noise ratio and this can make reliable detection very difficult.

It is accordingly desirable to provide alternative detection apparatus.

The subject matter discussed in this background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions.

SUMMARY OF THE INVENTION

According to one aspect of the present invention there is provided a detection apparatus of the above-specified kind, characterized in that the detection apparatus is arranged to establish a volume of analyte outside the detection apparatus and to supply analyte from the volume into the detection apparatus via an aperture in bursts smaller than that of the volume separated by periods when no analyte gas or vapor is admitted.

The detection apparatus preferably includes a preconcentrator by which the volume of analyte outside the apparatus is established. The preconcentrator may include polydimethylsiloxane. The detection apparatus preferably includes a pressure pulser connected with the interior of the detection apparatus by which the bursts of analyte are supplied into the detection apparatus. The detection apparatus may be an IMS, with the aperture opening into a reaction region and the reaction region opening into a drift region.

According to another aspect of the present invention there is provided a method of detecting an analyte sample gas or vapor, characterized in that the method includes the steps of establishing a volume of analyte, admitting bursts of analyte molecules less than the established volume to a reaction region, with the bursts being separated by periods of time during which substantially no analyte molecules are admitted, and detecting the presence of the admitted analyte molecules.

The volume of analyte is preferably established by adsorption and desorption. The analyte is preferably adsorbed while there is substantially no flow into the reaction region, with the analyte being subsequently desorbed and pressure momentarily reduced to draw desorbed analyte molecules into the reaction region. The pressure may be repeatedly reduced to draw a plurality of sips of analyte molecules from the desorbed molecules progressively to deplete the analyte molecules in the volume. Analyte sample gas or vapor may be adsorbed again by preconcentration, and pressure reduction may be stopped when the concentration of analyte in the volume has been depleted to an extent where analysis becomes less reliable, with desorption and pressure reduction being restarted again after sufficient time for detectable amounts of analyte to be released.

DESCRIPTION OF THE DRAWING

An IMS apparatus that is constructed and operated according to the present invention will now be described, by way of example, with reference to the accompanying FIGURE which shows IMS apparatus schematically.

DETAILED DESCRIPTION OF THE PREFERRED EMBODIMENT

With reference to the FIGURE, the detection apparatus takes the form of an ion mobility spectrometer ("IMS") having a generally tubular housing 1 with an analysis or drift region 2 towards its right-hand end (as shown in the FIGURE) and an ionization or reaction region 3 towards its opposite left-hand end (as shown in the FIGURE).

An inlet conduit 4 opens at one end 5 to air or another source of gas or vapor to be sampled and analyzed. At its other end, the inlet conduit 4 connects with a pump 17, by which the sample is drawn through the inlet conduit 4, and an aperture 6 provided by a capillary passage or pin-hole, which communicates between the inlet conduit 4 and the interior of the reaction region 3 so that molecules of interest can pass from the inlet conduit 4 into the reaction region 3. The aperture 6 could be provided by a membrane or other similar apparatus. The inlet conduit 4 includes a preconcentrator 7 or other similar apparatus for establishing a volume of analyte gas or vapor, the purpose of which will be described later.

The reaction region 3 contains apparatus to ionize molecules of the analyte substance, such as a corona discharge point 10, at a high potential. The reaction region 3 and the drift region 2 are both at atmospheric pressure or just slightly below atmospheric pressure. The reaction region 3 and the drift region 2 may be separated from one another by an optional, conventional electrostatic shutter 11 such as a Bradbury Nielson gate by which the flow of ions into the drift region 2 may be controlled. The drift region 2 has a series of pairs of electrodes 12 on opposite sides thereof which are longitudinally spaced from one another along the length of the drift region 2. A voltage supply 13 applies a voltage to each electrode pair 12, which voltage increases from the left to the right along the length of the drift region 2 (as shown in the FIGURE) so that ions passed by the electrostatic shutter 11 are subject to a voltage gradient, which draws them along the length of the drift region 2. A collector plate 14 mounted at the far, right-hand end of the drift region 2 (as shown in the FIGURE) collects ions after passage along the drift region 2. The charge produced by each ion when it impacts the collector plate 14 is supplied as an electrical signal to a processor unit 15. The processor unit 15 analyzes the signals to produce spectra representative of the mobility of the different ions detected and supplies these to a display or other utilization apparatus 16.

A gas flow system 20 provides a flow of clean dry air along the inside of the housing 1 against the flow of the ions. The gas flow system includes a pump 21 with molecular sieve inlet and outlet filters 22 and 23 respectively located at its inlet and outlet. The inlet filter 22 connects with an inlet pipe 24, which opens into the housing 1 towards the inlet end of the reaction region 3 (shown on the left end in the FIGURE). The outlet filter 23 connects with an outlet pipe 25, which opens into the housing 1 towards the downstream end of the drift region 2 (shown on the right end in the FIGURE). The pump 21 operates to draw gas from the reaction region 3 so that it flows through the first filter 22, the pump 21, and the second filter 23 before flowing back into the housing 1 at the right-most end of the drift region 2 (as shown in the FIGURE).

The apparatus also includes a pressure pulser 8, which may be an electromagnetic transducer similar to a loudspeaker, which is connected to the housing 1 in the manner described in U.S. Pat. No. 6,073,498, to Taylor et al., which is hereby incorporated herein by reference. The pressure pulser 8 is operated intermittently, momentarily to draw small volumes of sample vapor or gas into the reaction region 3 to produce a pressure pulse pattern of the kind illustrated.

The preconcentrator 7 includes a quantity of a material that will adsorb analyte vapor of interest and that can be arranged to desorb the vapor. A typical material that could be used is polydimethylsiloxane. Baffles could be arranged around the preconcentrator 7 to reduce sample losses due to diffusion. The preconcentrator 7 is located close to the aperture 6.

In operation, during the adsorption phase, air to be sampled is flowed into the conduit 4 by means of the pump 17 so that there is a continuous flow in and out of the conduit 4. During this adsorption phase, analyte vapor is adsorbed by the preconcentrator 7 and there is substantially no flow into the housing 1. The apparatus then goes through a desorption phase during which the pump 17 is turned off so that the inlet flow to the conduit 4 is stopped to prevent the collected sample from being blown away. The preconcentrator 7 is then heated or otherwise actuated to release the adsorbed analyte vapor into the volume 9 between the preconcentrator 7 and the aperture 6. At the same time, the pump 21 is turned off, or flow is substantially reduced, to prevent or reduce gas flow along the housing 1. The pressure pulser 8 is then activated to cause pulsed reductions in pressure within the housing 1. This has the effect of drawing in small bursts, puffs, or sips of the vapor in the volume 9 through the aperture 6 as jets into the reaction region 3. The vapor in each such burst is ionized in the reaction region 3, and ion mobility spectra are produced by the processor unit 15. The volume of each burst caused by the pressure pulser 8 is substantially less than the static volume of vapor established by the preconcentrator 7 in the volume 9. As such, the pressure pulser 8 can take many sips of the static vapor in the volume 9 before the concentration of the analyte in the volume 9 becomes depleted to an extent that the spectra produced become unreliable. When this happens, the detector reverts again to an adsorption phase.

By taking multiple sips from an established volume of analyte vapor, many spectra samples can be obtained, thereby enabling prolonged averaging and an increase in the signal-to-noise ratio. This is especially valuable where the analyte is only present in very low concentrations. The small sips of sample taken also avoid overloading the detector with excessive quantities of analyte substance where it is present in high quantities and enable the dynamic range of the detector apparatus to be extended. If the vapor concentration detected in the first burst is high, the detector apparatus could be arranged such that no further bursts are taken. Furthermore, the arrangement of the present invention avoids the problems that can occur when a high level of moisture is present, since this can prevent efficient ionization. By taking small bursts, the moisture is diluted to an extent such that it does not prevent detection of the compounds of interest.

Although it is preferable for gas flow within the housing 1 that are produced by the gas flow system 20 to be stopped when sample bursts are drawn into the reaction region 3, it is not essential to do so, since the flow could be maintained to flush away the sample burst, providing that the sample stays within the reaction region 3 sufficiently long for analysis to take place. It should also be noted that it is not necessary to stop gas flow along the entire housing 1, since the detection apparatus could have a separate gas flow path within the reaction region 3. In such an arrangement, this separate gas flow could be stopped, and the remaining flow along the drift region 2 could be maintained. In another arrangement, the gas flow could be stopped when each burst is taken, and then restarted between bursts to flush away the analyte substance. Alternatively, the flow of gas through the reaction region 3 could be stopped for a period extending over several discrete bursts.

There are various alternative ways in which a volume of sample substance could be established. Microelectromechanical systems ("MEMS") processes can be used to construct small chambers containing sorbent material onto which the vapor is adsorbed and from which it is desorbed.

Instead of using heat to desorb the adsorbed substance, it would be possible to use radiation, pressure, or vibration to encourage desorption, either by itself or in conjunction with some other process.

The present invention can be used to enable small concentrations of analyte to be detected with improved signal-to-noise ratio. The present invention is particularly useful in IMS apparatus, but may also have application in different forms of detectors.

Although the foregoing description of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

While the current application recites particular combinations of features in the claims appended hereto, various embodiments of the invention relate to any combination of any of the features described herein whether or not such combination is currently claimed, and any such combination of features may be claimed in this or future applications. Any of the features, elements, or components of any of the exemplary embodiments discussed above may be claimed alone or in combination with any of the features, elements, or components of any of the other embodiments discussed above.

What is claimed is:

1. A method of detecting or analyzing an analyte sample gas or vapor, comprising the steps of:
   establishing a volume of analyte by absorption and desorption;
   admitting bursts of analyte molecules less than the established volume to a reaction region, the bursts being separated by periods of time during which substantially no analyte molecules are admitted; and
   detecting the presence of the admitted analyte molecules.

2. The method defined in claim 1, wherein analyte is adsorbed while there is substantially no flow of analyte into the reaction region, and that analyte is subsequently desorbed and pressure is momentarily reduced to draw desorbed analyte molecules into the reaction region.

3. The method defined in claim 2, wherein pressure is repeatedly reduced to draw a plurality of sips of analyte molecules from the desorbed molecules progressively to deplete the analyte molecules in the volume.

4. The method defined in claim 3, wherein after the analyte molecules in the volume have been depleted analyte sample gas or vapor is adsorbed again by preconcentration and pressure reduction is stopped when the concentration of analyte in the volume has been depleted to an extent where analysis becomes less reliable, and that desorption and pressure reduction is restarted again after sufficient time for detectable amounts of analyte to be released.

5. A method of detecting or analyzing an analyte sample gas or vapor, comprising the steps of:
   establishing a volume of analyte outside the aperture with a preconcentrator;
   admitting analyte sample gas or vapor to a detection apparatus through an aperture from the volume of analyte outside the aperture; and
   energizing a pressure pulser connected with the interior of the detection apparatus momentarily to drop pressure in the detection apparatus to draw analyte from the volume into the detection apparatus via the aperture in bursts smaller than that of the volume between periods when the pressure pulser is not energized during which periods no analyte gas or vapor is admitted.

6. The method defined in claim 5, wherein the preconcentrator comprises polydimethylsiloxane.

7. The method defined in claim 5, wherein the detection apparatus is operated in a manner to function as an ion mobility spectrometer, wherein the aperture opens into a reaction region, and wherein the reaction region opens into a drift region.

8. The method defined in claim 5, additionally comprising the step of:
   controlling the passage of analyte from the volume into the detection apparatus solely by the operation of the pressure pulser.

9. A method of detecting or analyzing an analyte sample gas or vapor, comprising the steps of:
   providing a detection apparatus housing having a first end at which an analyte will be admitted to the detection apparatus housing and a second end opposite the first end, the detection apparatus housing comprising:
      a reaction region located in the detection apparatus housing adjacent the first end thereof; and
      a drift region located in the detection apparatus housing between the reaction region and the second end of the detection apparatus housing;
   supplying an analyte to a first end of an inlet conduit;
   establishing a volume of analyte in the inlet conduit adjacent a second end thereof;
   momentarily energizing a pressure pulser connected with the interior of the detection apparatus housing to drop pressure in the interior of the detection apparatus housing; and
   admitting an analyte sample from the second end of the inlet conduit into the reaction region in the detection apparatus housing via an aperture in bursts smaller than that of the volume whenever the pressure pulser is energized momentarily to drop pressure in the detection apparatus separated by periods when the pressure pulser is not energized during which periods no analyte is admitted into the reaction region in the detection apparatus housing.

10. The method defined in claim 9, additionally comprising:
    establishing the volume of analyte outside the aperture intermediate a preconcentrator located in the inlet conduit and the second end of the inlet conduit.

11. The method defined in claim 10, wherein the preconcentrator includes a material comprising:
    polydimethylsiloxane.

12. The method defined in claim 9, additionally comprising the step of:

operating the pressure pulser to repeatedly reduce pressure in the detection apparatus housing to draw a plurality of sips of analyte sample in the volume.

13. The method defined in claim 9, additionally comprising the steps of:
    adsorbing the analyte with a material during the periods of time during which substantially no analyte molecules are admitted to the reaction region; and
    desorbing the analyte during the periods of time when analyte samples are admitted to the reaction region in bursts.

14. The method defined in claim 9, additionally comprising the step of:
    ionizing molecules of the analyte gas or vapor that has been admitted to the reaction region with an ionizing apparatus located in the reaction region.

15. The method defined in claim 9, additionally comprising the step of:
    controlling the flow of ions from the reaction region to the drift region with an electrostatic shutter.

16. The method defined in claim 9, additionally comprising the step of:
    establishing an electrical field in the drift region with a plurality of longitudinally spaced-apart electrode pairs located in the drift region which electrical field draws ions located in the drift region in a direction from the first end of the detection apparatus housing to the second end of the detection apparatus housing.

17. The method defined in claim 9, additionally comprising the steps of:
    collecting ions passing to the second end of the detection apparatus housing with a collector plate located near the second end of the detection apparatus housing; and
    providing an output to a processor indicative of the ions detected by the collector plate.

18. The method defined in claim 9, additionally comprising the step of:
    controlled the passage of analyte from the volume into the detection apparatus solely by the operation of the pressure pulser.

\* \* \* \* \*